United States Patent [19]
Melman et al.

[11] Patent Number: 5,903,348
[45] Date of Patent: May 11, 1999

[54] SYSTEM AND METHOD FOR MOLECULAR SAMPLE MEASUREMENTS

[75] Inventors: Paul Melman, Newton; Marvin Tabasky, Peabody, both of Mass.

[73] Assignee: NZ Applied Technologies, Inc., Woburn, Mass.

[21] Appl. No.: 08/815,219

[22] Filed: Mar. 12, 1997

[51] Int. Cl.⁶ .................................................. G01N 21/00
[52] U.S. Cl. ........................................... 356/344; 204/451
[58] Field of Search .................................. 356/374, 73.1, 356/441, 246; 385/15, 37, 39, 49, 50, 59, 71, 88, 89; 204/451, 452, 603, 180.1

[56] References Cited

U.S. PATENT DOCUMENTS

| | | | |
|---|---|---|---|
| 4,639,074 | 1/1987 | Murphy | 350/96.15 |
| 4,729,947 | 3/1988 | Middendorf et al. | 435/6 |
| 4,927,265 | 5/1990 | Brownlee | 356/73 |
| 5,114,551 | 5/1992 | Hjerten et al. | 204/180 |
| 5,274,240 | 12/1993 | Mathies et al. | 250/458 |
| 5,312,535 | 5/1994 | Waska et al. | 204/299 |
| 5,324,401 | 6/1994 | Yeung et al. | 204/180 |
| 5,359,686 | 10/1994 | Galloway et al. | 385/49 |
| 5,439,578 | 8/1995 | Dovichi et al. | 204/299 |
| 5,498,324 | 3/1996 | Yeung et al. | 204/452 |
| 5,516,409 | 5/1996 | Kambara | 204/603 |
| 5,580,471 | 12/1996 | Fukumoto et al. | 219/121 |
| 5,582,705 | 12/1996 | Yeung et al. | 204/603 |
| 5,583,736 | 12/1996 | Anderson et al. | 361/234 |

OTHER PUBLICATIONS

O'Donnell, Thomas R., "Genetic Reader", The Des Moines Registry, (Jul. 1995).
Yeung, M.D., Edward, "Superfast, Highly Accurate DNA Sequencer to be Commercially Available in 1996", Ames Laboratory (Jul. 1995).
Borman, Stu, "Developers of Novel DNA Sequencers Claim Major Performance Advances", C&EN Washington, Jul. 1995).
Taylor, John A. and Yeung, Edward A., "Multiplexed Fluorescence Detector for Capillary Electrophoreses Using Axial Optical Fiber Illumination", Anal. Chem. 1993 65, 956–960.
Ueno, Kyoll and Yeung, Edward S., "Simultaneous Monitoring of DNA Fragments Separated by Electrophoresis in a Multiplexed Array of 100 Capillaries", Anal. Chem. 1994, 66, 1424–1431.
Fung, Elize N. and Yeung, Edward S., "High–Speed DNA Sequencing by Using Mixed Poly(ethylene oxide) Solutions in Uncoated Capillary Columns", Anal Chem 1995, 67, 1913–1919.

*Primary Examiner*—Frank G. Font
*Assistant Examiner*—Michael P. Stafira
*Attorney, Agent, or Firm*—Hamilton, Brook, Smith & Reynolds, PC

[57] ABSTRACT

A system for aligning the optical components of a chemical analysis system in which capillaries or optical fibers are supported by a micromechanied substrate. The system provides for alignment of elements of an electrophoresis system in an efficient high sampling rate capability.

28 Claims, 6 Drawing Sheets

SYSTEM AND METHOD FOR MOLECULAR SAMPLE MEASUREMENTS

BACKGROUND

Capillary Gel Electrophoresis (CGE) is a sensitive method for analysis and identification of biological molecular systems. CGE is a relatively new analytical separation technique that can be applied to the analysis of a wide variety of compounds that provide for improved resolution over other existing techniques. Its use for increasing the rate at which DNA sequencing can be performed has been of particular interest. Because of its sensitivity, the technique is gaining acceptance in many laboratories and manufacturing operations of drug and chemical manufacturers worldwide. However, the instrumentation that is being used to produce the data using this technique is still relatively inefficient, complex and expensive. Although these systems can appear physically different from each other, they all contain the basic functional blocks required for this type of analysis. Each has a method of holding the capillaries, injecting samples therein, transmitting and collecting light, detecting a fluorescent signal from each sample being measured that is induced by the incident light energy, applying voltage to the capillaries, and outputting the collected data in some form.

What these systems generally suffer from is that the techniques involve equipment that is not cost effective for high volume manufacturing, and consequently does not permit widespread use of this important analytical technique. The performance of a single capillary system depends on the method of sample excitation and on the signal collecting optics. In multi-capillary systems precise alignment of delivery collection and sample assemblies can be difficult. In free beam systems this has been done by visual inspection of reflected or transmitted laser light.

There is a continuing need for improvements in systems for performing optical measurements of biological samples that are readily manufacturable, have low maintenance costs and provide for fast accurate analysis of a large number of samples.

SUMMARY OF THE INVENTION

This invention relates to a system and method for delivering light to chemical or biochemical samples using an aligned optical fiber delivery system that couples light from a light source with an array of sample channels. Light from the samples is collected and detected for data analysis, presentation, and storage. The optical signal collection is accomplished by a second optical fiber system. In a preferred embodiment, the delivery and collection optical fiber systems are mounted and permanently aligned on a mounting structure such that each Capillary is in the same plane as the delivery fiber and collection fiber for that capillary. The delivery and collecting fibers can be selected with respect to their core sizes and numerical apertures to satisfy the particular application requirements. The collecting fiber largely filters out the excitation light, reducing the detection noise and improving the detection sensitivity. A multi-mode fiber can be used for this purpose. In an optical fiber CGE delivery and collection system, the collecting fiber fulfills the role of a spatial filter, lens and a light guide. The two fibers and the capillary are co-planar, enabling a practical and inexpensive method of fabricating a multichannel assembly. The spatial filtering of the undesired, noise-generating, excitation light in the collecting fiber has improved performance over free beam systems where reflections dominate the flourescence signal.

This fiber optical system presents a number of advantages over the free beam technology used in existing systems. There are no optical components other than fibers, thereby reducing cost, complexity and size. Also, the geometry reduces the amount of excitation light reflected back to the collecting fiber, improving signal to noise ratio. Another advantage of this fiber system is simplification of multicolor detection in comparison with free beam optics where the focal length of lenses, or deflection angles are wavelength sensitive, making simultaneous focusing of different colors difficult. This is not the case in a fiber based system where the emitted light fills substantially the same cone of light at the fiber output and input.

A preferred embodiment of the invention pertains to all fiber systems where the fiber and capillary assemblies are fabricated by affixing them on precision planar surfaces. This relies on highly precise features or grooves formed on a silicon wafer or substrate, for example, by well known micromachining techniques. A large number of capillaries can be precisely aligned and measured with this system and thereby substantially increase the rate of sample analysis. Features are accurate to within 10 microns or less to provide the accurate positioning necessary to achieve the desired measurement accuracy.

Alignment features can also be incorporated in the substrates. An optical alignment system is described here where an alignment accuracy of less than 10 microns, and preferably of about 1 um is employed. This method makes use of the precise geometry of the fiber and capillary assembly substrates.

The registration feature can be a single or a multiple groove structure depending on the method used. The optical registration technique makes use of detecting a change in surface reflectivity when a fiber tip moves over a groove or a similarly reflecting feature in the reflecting surface. If the fiber position is fabricated precisely with the reflecting feature the change of reflectivity indicates the point of registration.

Another preferred embodiment of the invention includes a system and method for positioning an optical fiber relative to a measurement cell such as a capillary tube. In this system light emitted by an optical fiber and is reflected by the capillary surface, for example, and the intensity of the sensed reflected signal is compared to a reference value. The comparison is used to stop the motion of the optical fiber system when it is correctly positioned. A feedback control system can be used to automatically position either the optical fiber system, or the capillary system, relative to the other.

DETAILED DESCRIPTION

Figure 1:
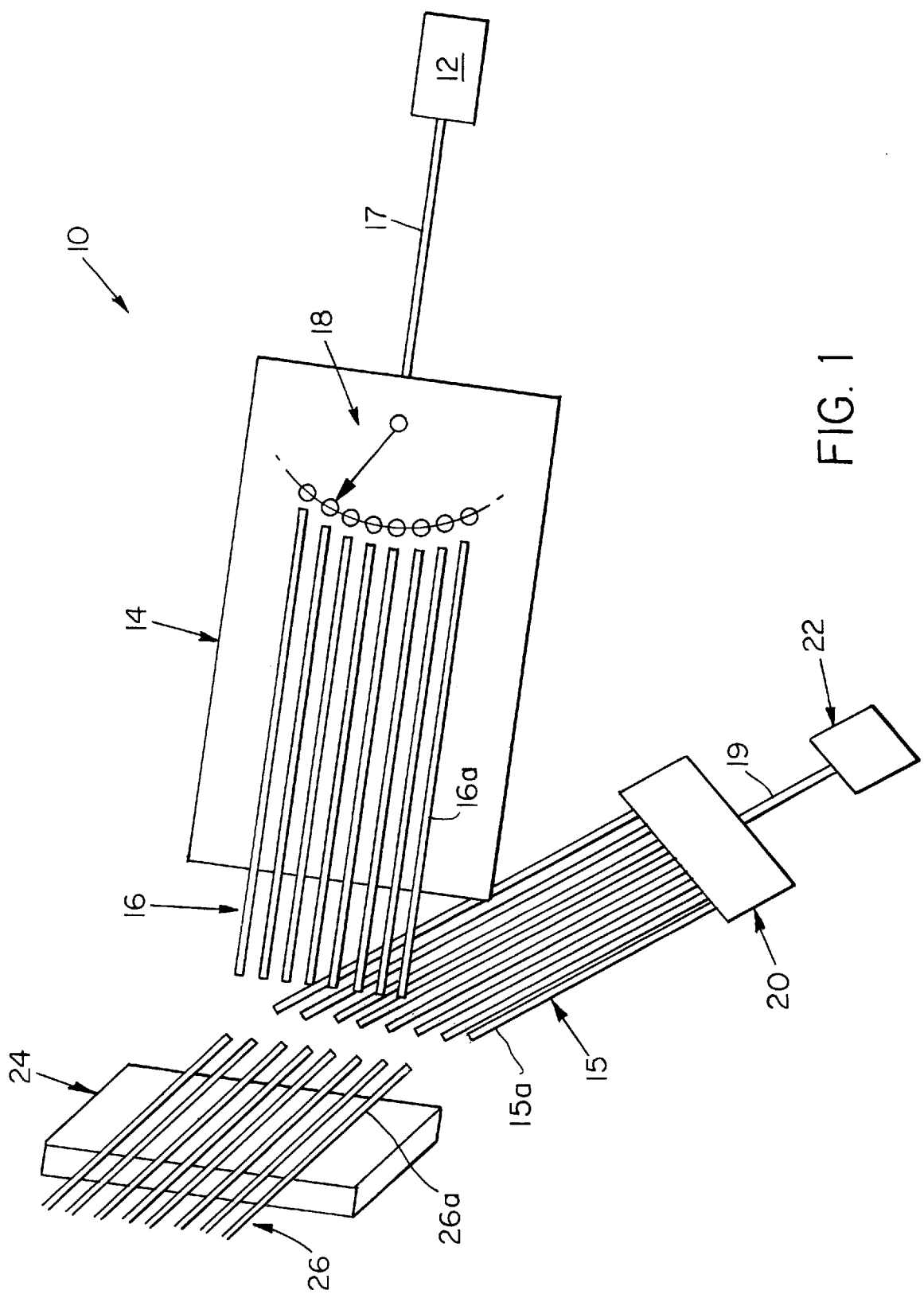
FIG. 1 illustrates a system for optically measuring the contents of a capillary array in accordance with a preferred embodiment of the invention.

A preferred embodiment of the invention is illustrated in the CGE system 10 of FIG. 1. An array of capillaries 26 is provided that are mounted on a first substrate 24. An array of delivery fibers 16 is mounted on a substrate 14 and an optical switch 18 is positioned to couple light from light source 12 to each of the fibers 16 in sequence. Light source 12 can preferably be an argon laser, a solid state laser or any other light source having a suitable emission spectrum for a given application. The light source is coupled to optical switch 18 with a fiber 17. The system also includes an optical combiner or second switch 20 that is coupled to a detector 22 such as a photomultiplier tube or solid state detector device such as a charge coupled device or CMOS detector. As described below the detector is connected to a multichannel analyzer 21, a computer 23 and display 25.

In operation, light from the source is coupled to fibers 16 in sequence. The distal ends of the fibers are each in close proximity to a window on a capillary tube. In a preferred embodiment of the system, each capillary has a corresponding delivery and collection fiber. Each capillary, 26a for example, is in a single plane with its corresponding delivery 16a and collection 5a fiber. This provides a compact system providing for easy alignment.

A mounting structure 150 for the optical fiber system of the present invention is illustrated in connection with FIG. 2. The delivery fibers 16 are mounted onto a precision grooved substrate 14 with an adhesive layer 39. The substrate 14 is mounted onto a mounting element 140 with the fibers extending between the substrate 14 and a first mounting surface of element 140. The collection fibers 15 and second substrate are similarly mounted on a second mounting surface of element 140. The mounting surface define an angle such that the delivery and collection fibers are at an angle between 40° and 50° relative to each other, preferably at about 45°. Smaller angles tend to increase the signal to noise ratio and higher angles tend to tighten the alignment tolerances.

The element 140 can be mounted on a moveable platform or support in which a first actuator 33 and a second actuator 35 can be used to either manually or electromechanically reposition the optical fiber system relative to the capillaries 26. An alignment fiber 29 coupled to a second light source such as a light emitting diode 27 and light sensor 28 can be used for registration. Servo motors can be connected along circuit 37 to computer 23 or other controller to provide for automatic feedback control of the fibers relative to the capillary assembly.

Figure 3:
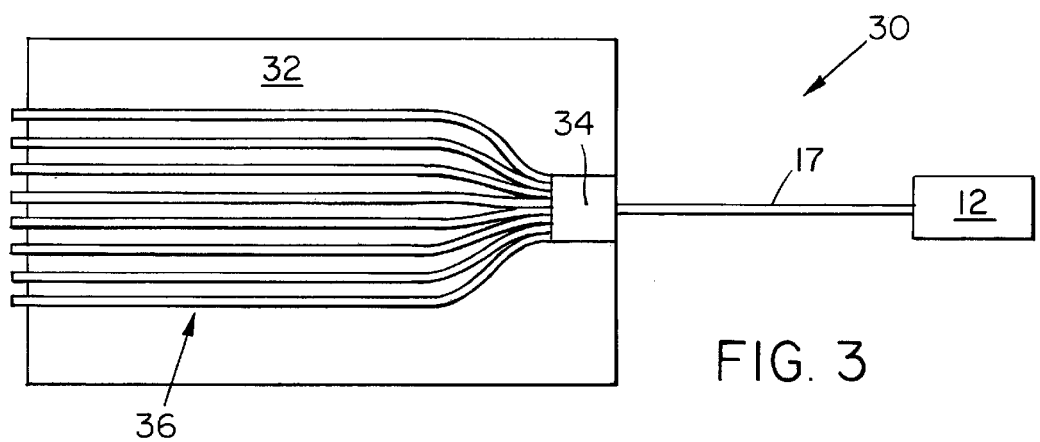
FIG. 3 illustrates an alternative embodiment of the invention using an optical splitter for simultaneous irradiation of capillaries.

In another preferred embodiment the optical switch is replaced by an optical splitter 34 as shown in the illustration of the light delivery system 30 in FIG. 3. In this embodiment, light from the source 12 is delivered through fiber 17 to a splitter, which in the embodiment divides the light into eight separate components and couples the light components into the proximal ends of fibers 36. The fibers 36 are mounted onto the channels of a substrate 32 as described in greater detail below. In this embodiment, although the power requirements for light source 12 are substantially increased, the samples of all eight capillaries that are coupled to the fibers 36 can be measured simultaneously.

A preferred method for fabricating the substrates 14 and 24 is illustrated in connection with the process flow sequence 40 of FIG. 4. In this particular example, a silicon wafer is provided 42 having suitable resistivity, thickness, diameter and crystallographic orientation. The wafer can be cleaned 44 with a mixture of sulfuric acid and water and revised. A masking layer is then deposited 46, preferably a one micron thick layer of silicon nitride using a low pressure chemical vapor deposition process. Next a photolithographic step 48 is performed by depositing and patterning a photoresist to define the channel or groove structure to be formed in the wafer. Note that several patterns can be formed in a single wafer. The linewidths of the resist pattern are then verified and the silicon nitride layer is etched 50 to expose the surface pattern for the grooves in the wafer. The photoresist is then removed and the linewidth of the openings in the silicon nitride layer are measured.

If the pattern is satisfactory, the exposed silicon is etched 52 using a standard etchant, such as a KOH/Alc mixture at 80° C. The remaining silicon nitride can be removed 54 using an HF bath and the wafer surface is rinsed to the desired resistivity.

The grooved silicon substrate can be oxidized 56 to provide an insulting layer having a thickness in the range of 5,000 to 10,000 Angstroms. This can be performed in a thermal oxidation furnace at 950° C.

The wafer or substrate is then diced or cut 58 with a saw to provide a plurality of grooved substrates having desired geometrics.

Note that a large number of 8 or 16 groove substrates can be fabricated and affixed to a frame to provide a large number of capillary elements. As many as 96 or more capillaries can be configured in a single system. One or a plurality of lasers can be used depending upon the number of capillaries, the switching capacity and power requirements.

Figure 5:
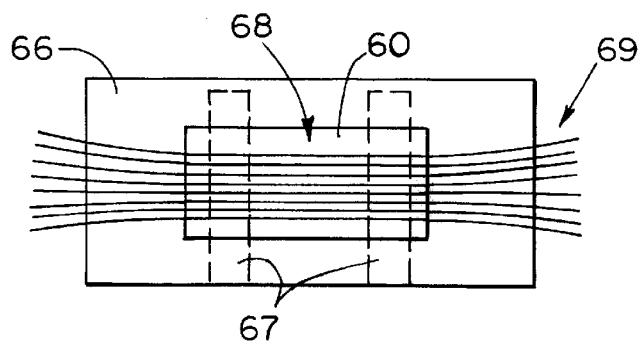
FIG. 5 is a top view of a system for mounting guides onto a channeled substrate in accordance with the invention.

Illustrated in FIG. 5 is an assembly used to mount guides such as optical fibers or capillaries 69 into the channels of a substrate 60. The substrate 60 is held by a vacuum chuck on a supporting surface 66 and two arms 67 are positioned over to guides 69 to hold them in the grooves.

An adhesive such as a UV curable commercially available epoxy is placed into the opening 68 between the arms 67 and cured. The arms 67 are then removed and the substrate released from the support 66. This provides a procedure well suited for automated manufacture of registered guide components for optical measurement systems.

Figure 4:
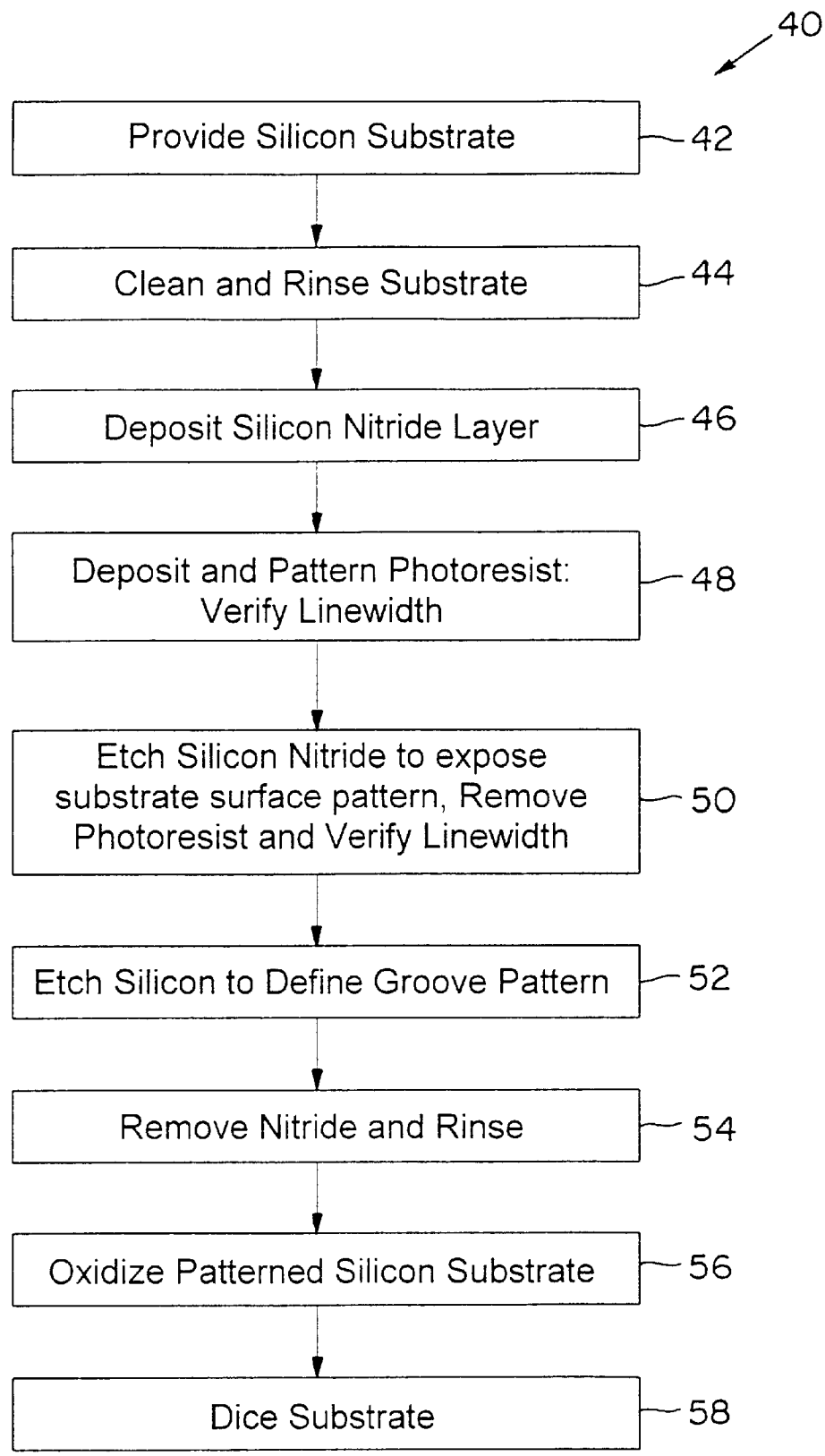
FIG. 4 illustrates a process sequence for making a multi-capillary holder in accordance with a preferred embodiment of the invention.
Figure 6:
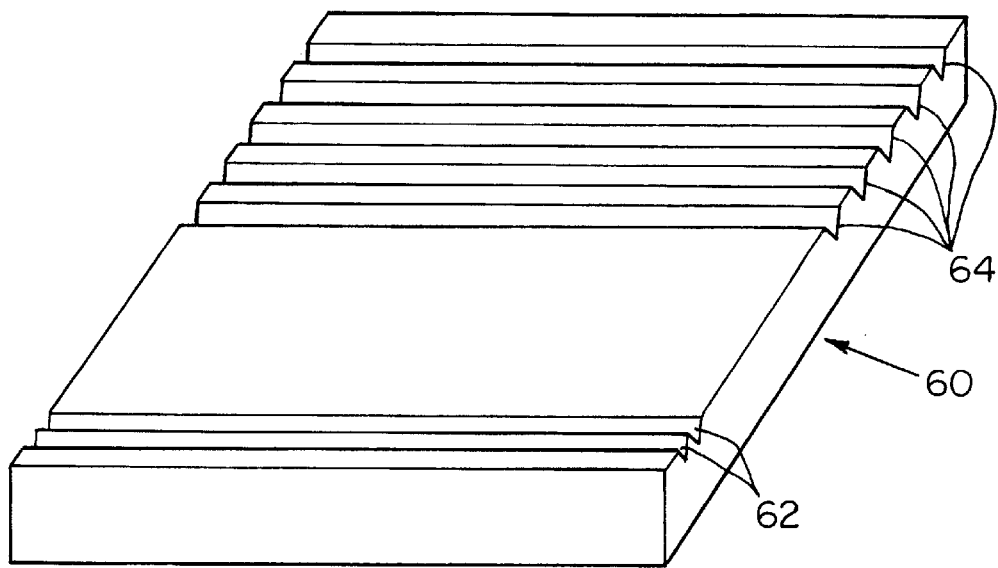
FIG. 6 shows a grooved silicon substrate made in accordance with the method of FIG. 3.

A typical substrate 60 fabricated in accordance with the method of FIG. 4 is illustrated in FIG. 6. The substrate 60 has grooves or channels 64 for holding optical fibers or capillary tubes. Alignment grooves 62 can also be included and used for alignment as shown in FIGS. 8A and 8B below.

Figure 2:
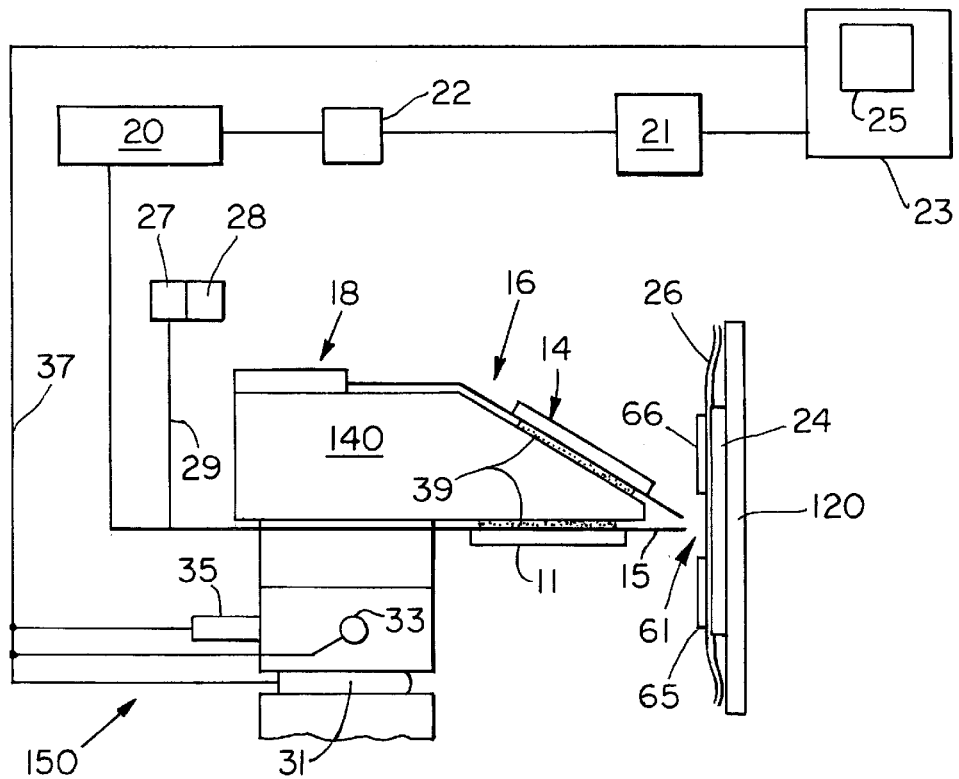
FIG. 2 is a detailed view of the fiber optic delivery and collection system in accordance with the invention.
Figure 7:
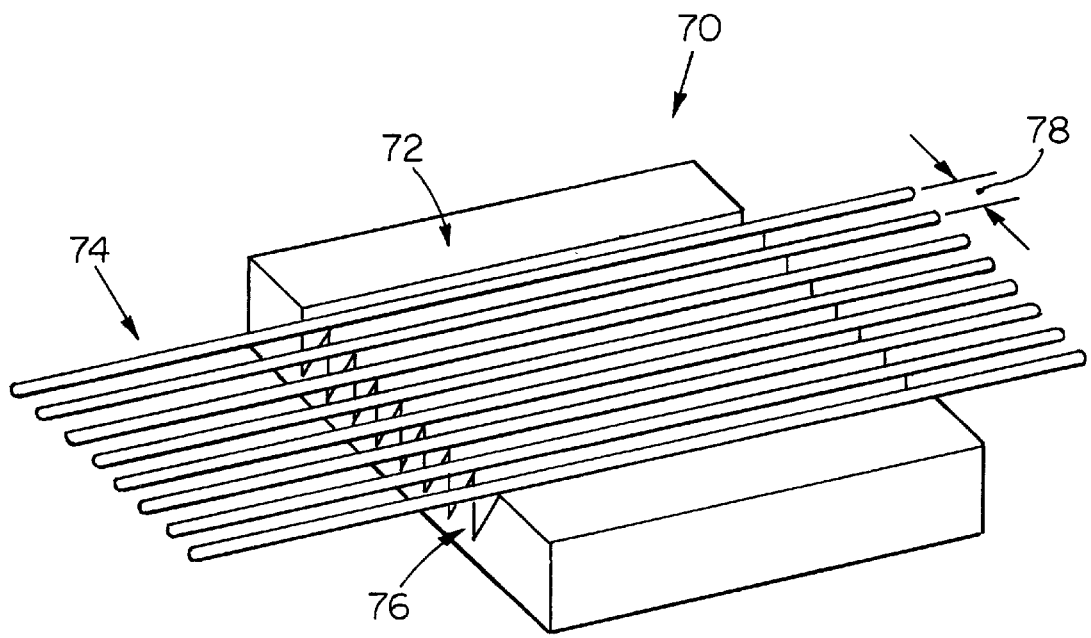
FIG. 7 illustrates an array of capillaries or fibers mounted on a grooved silicon substrate.

FIG. 7 illustrates an alignment module 70 that can be used in the system of FIGS. 1 and 2. The substrate 72 has grooves 76 in which capillary tubes or fibers 74 have been positioned. The distance 78 between adjoining fibers or capillaries is precisely known.

Figure 8A:
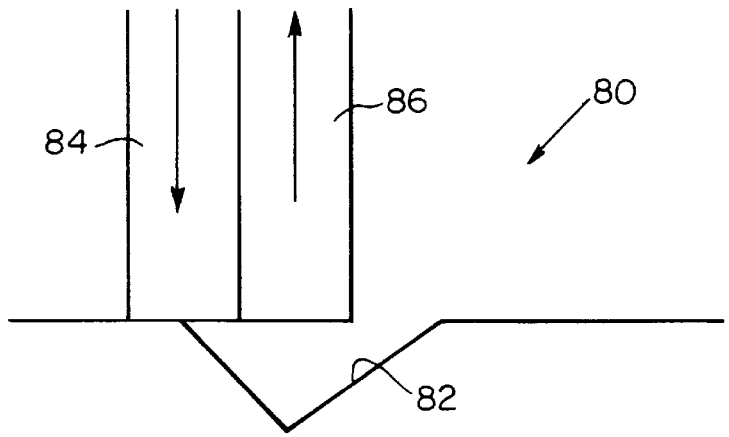
FIGS. 8A and 8B illustrate methods for aligning arrays with a fiber optic device.
Figure 8B:
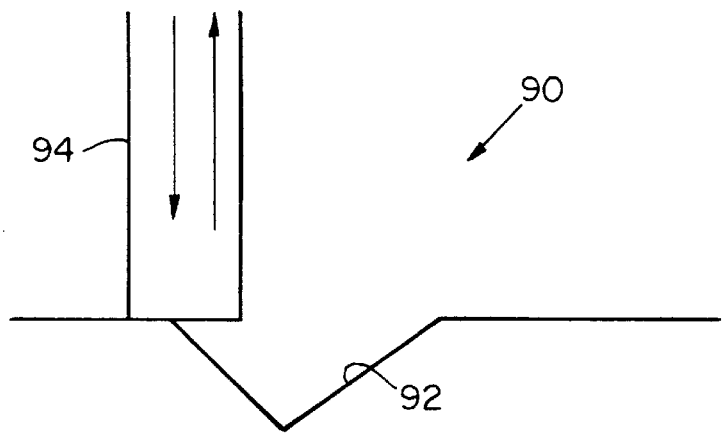

As shown in FIGS. 8A and 8B a two fiber system 80 or single fiber system 90 can be used with a groove 82, 92, respectively, in a substrate to confirm alignment. In system 80 fibers 84 and 86 are used to deliver or collect light from a reflecting feature 82 such as a groove. A detector coupled to the proximal end of fiber 86 will verify alignment. Alternatively, in the single fiber system the reflected signal will null out to indicate a proper registration mark.

Figure 9:
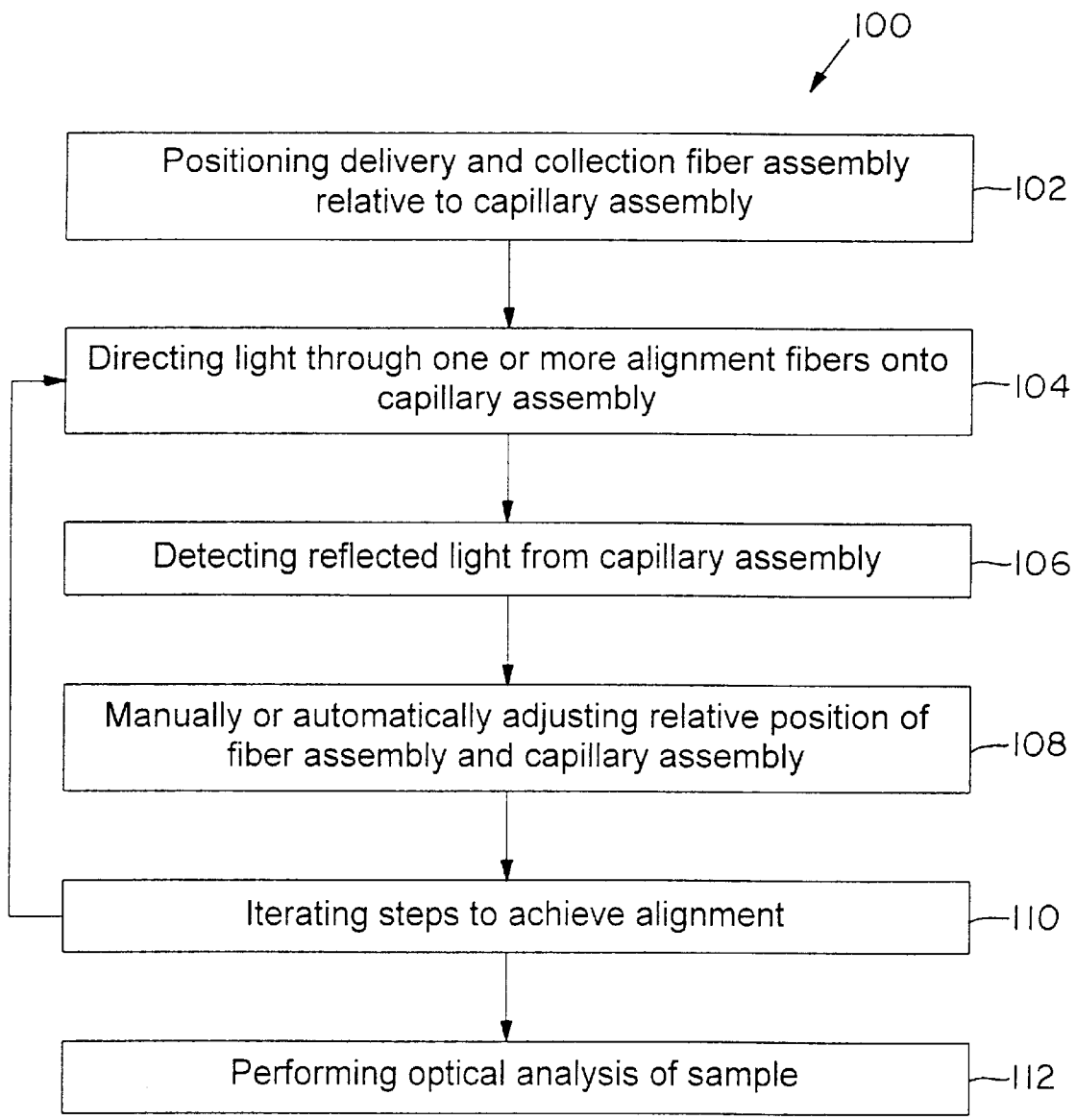
FIG. 9 is a preferred process for aligning the optical elements of an optical analysis system in accordance with the invention.

This process is illustrated in connection with the process sequence of FIG. 9. After initial assembly of the fibers onto element 140 the optical fiber system is positioned 102 relative to the capillaries using visual inspection. Light is directed 104 through one or more alignment fibers onto the capillary assembly and the reflected light is detected 106. Based upon this measurement, the element 140 is repositioned 108 and the light delivery and detection steps are repeated 110 until the capillaries are properly aligned and sample analysis 112 can be performed.

Figure 10:
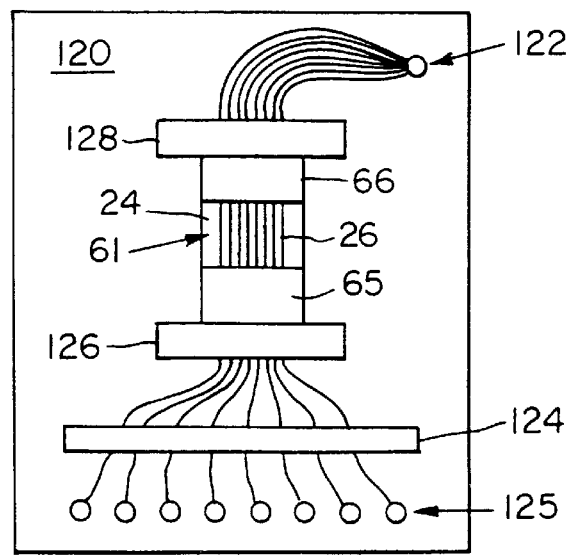
FIG. 10 is a mounting structure for a capillary assembly in accordance with the invention.

Shown in FIG. 10 is a capillary assembly including a support 120, two arms 124 and 128 to hold the capillary substrate onto the support 120, electrical leads 125 to connect to first ends of each capillary, and a capillary holder 124. A common electrical lead 122 can be used to connect the second end of the capillaries to a common electrical connector 122. The capillary assembly can also include silicon panels 65, 66 or the opposite side of the optical fibers relative to substrate 24. The substrate 24 and panels 65, 66 act as a heat sink to remove heat from the capillaries caused by the current passing through them. This prevents thermally induced movement of the capillaries that may result in misalignment relative to the optical fiber system.

Equivalents

While this invention has been particularly shown and described with reference to preferred embodiments thereof, it will be understood by those skilled in the art that various changes in form and details may be made therein without departing from the spirit and scope of the invention as defined by the appended claims.

We claim:

1. A capillary analysis system comprising:
    a light source;
    a fiber optic delivery system coupled to the light source, the fiber optic delivery system including a plurality of delivery optical fibers;
    a plurality of capillaries, each capillary being positioned to receive light through an optical fiber of the delivery system from the light source;
    a fiber optic collection system to receive light from the capillaries, the fiber optic collection system including a plurality of collection optical fibers such that the plurality of capillaries, the fiber optic delivery system and the fiber optic collection system provide a plurality of optical paths;
    a detector optically coupled to the fiber optic collection system; and
    an alignment substrate on which each of the delivery optical fibers are mounted such that each of the delivery optical fibers is aligned with a respective capillary.

2. The system of claim 1 wherein the substrate comprises a silicon substrate having a plurality of channels.

3. The system of claim 1 further comprising a capillary substrate including a silicon substrate having a plurality of channels.

4. The system of claim 1 wherein each optical path comprises a delivery optical fiber, a capillary and a collection optical fiber positioned in a single plane.

5. The system of claim 1 wherein the light source comprises a laser.

6. The system of claim 1 wherein the fiber optic delivery system comprises optical fibers positioned in channels in the substrate.

7. The system of claim 1 further comprising a mounting element on which the delivery system optical fibers and the collection system optical fibers are mounted.

8. The system of claim 1 wherein each capillary is aligned with one of the delivery optical fibers and one of the collection optical fibers in a common plane.

9. The system of claim 8 wherein each delivery optical fiber and each collection optical fiber are aligned with one of the capillaries and are positioned on a first side of said capillary, the capillary being mounted on a second side of the capillary on a capillary substrate.

10. A capillary analysis system comprising:
    a light source;
    a fiber optic delivery system coupled to the light source, the delivery system including a plurality of delivery optical fibers;
    a plurality of capillaries that receive light through the delivery system from the light source;
    a fiber optic collection system that receives light from the capillaries, the collection system including a plurality of collection optical fibers;
    a detector optically coupled to the fiber optic collection system;
    a first substrate on which the delivery optical fibers are mounted to position an end of each delivery optical fiber relative to one of the capillaries; and
    a second substrate on which the collection optical fibers are mounted to position an end of each collection optical fiber relative to one of the capillaries.

11. The system of claim 10 wherein the first substrate comprises a silicon substrate having a plurality of channels.

12. The system of claim 11 wherein the capillaries are positioned in channels of a third substrate.

13. The system of claim 10 wherein each delivery optical fiber, a respective capillary and a respective collection optical fiber are positioned in a single plane.

14. The system of claim 10 wherein the light source comprises a laser coupled to an optical switch or an optical splitter, the switch or splitter being optically coupled to proximal ends of the delivery system optical fibers.

15. The system of claim 10 wherein the delivery optical fibers are positioned in channels in the first substrate.

16. The system of claim 10 wherein the first substrate and the second substrate are positioned on a mounting element.

17. The system of claim 16 wherein the mounting element positions the first substrate at an angle between 40° and 50° relative to the second substrate.

18. The system of claim 10 further comprising a second light source coupled to an alignment optical fiber such that light from the alignment optical fiber is detected by a light sensor, to determine registration between the delivery system and the capillaries.

19. The system of claim 16 further comprising an actuator such that the mounting element can be moved relative to the capillaries.

20. A method of capillary analysis comprising:

aligning a distal end of each of a plurality of delivery optical fibers relative to a capillary assembly;

emitting light from a distal end of each of the optical fibers such that light from the optical fibers is directed onto the capillary assembly; and detecting light from the capillary assembly with a plurality of collection optical fibers, each collection optical fiber being optically coupled to a capillary in the capillary assembly.

21. The method of claim 20 further comprising the step of comparing an intensity value of the detected light to a reference value.

22. The method of claim 20 further comprising coupling a light emitting diode to an optical fiber.

23. The method of claim 20 further comprising determining a component of material in the capillary.

24. The method of claim 20 further comprising providing a controller connected to the detector and a fiber alignment system.

25. The method of claim 20 further comprising providing a detector coupled to a proximal end of a collection optical fiber.

26. The method of claim 20 further comprising providing a mounting element on which the delivery optical fibers and collection optical fibers are mounted.

27. The method of claim 26 further comprising moving the mounting element to align the delivery and collection fibers with the capillaries.

28. The method of claim 20 further comprising providing a first substrate on which the delivery optical fibers are mounted and providing a second substrate on which the collection optical fibers are mounted.

* * * * *